(12) United States Patent
Carina et al.

(10) Patent No.: US 6,696,403 B2
(45) Date of Patent: Feb. 24, 2004

(54) COMPOSITION AND METHOD FOR BLEACHING A SUBSTRATE

(75) Inventors: Riccardo Filippo Carina, Geneva (CH); Michel Gilbert Jose Delroisse, Vlaardingen (NL); Ronald Hage, Vlaardingen (NL); David Tetard, Merseyside (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 66 days.

(21) Appl. No.: 10/067,665

(22) Filed: Feb. 5, 2002

(65) Prior Publication Data

US 2003/0008796 A1 Jan. 9, 2003

(30) Foreign Application Priority Data

Feb. 5, 2001 (GB) .............................................. 0102826

(51) Int. Cl.[7] .......................... C11D 3/00; C11D 3/395; C11D 7/18; C11D 7/54
(52) U.S. Cl. ...................... 510/309; 510/302; 510/375
(58) Field of Search ................. 510/302, 309, 510/375

(56) References Cited

U.S. PATENT DOCUMENTS 5,250,401 A * 10/1993 Okada et al. ............... 430/393

FOREIGN PATENT DOCUMENTS

| EP | 1 001 009 | 11/1998 |
|----|-----------|---------|
| WO | 99/65905 | 12/1999 |
| WO | 00/12667 | 3/2000 |
| WO | 00/12808 | 3/2000 |
| WO | 00/29537 | 5/2000 |
| WO | 00/60043 | 10/2000 |
| WO | 00/60045 | 10/2000 |

OTHER PUBLICATIONS

American Chemical Society, 1989, pp. 9039–9047; Gomez–Romero et al., "Dissymmetry Effects in $\mu$–Oxo Diiron (III) Species: Structures and Spectroscopie Properties of $[N5FeOFeX_3]^+$ (X=Cl, Br) and Implications for Oxo–Bridged Dinuclear Iron Proteins"; XP–002207358.

* cited by examiner

Primary Examiner—Yogendra N. Gupta
Assistant Examiner—John M. Petruncio
(74) Attorney, Agent, or Firm—Milton L. Honig

(57) ABSTRACT

The invention relates to catalytically bleaching substrates, especially laundry fabrics, with a bleaching composition using either air or a peroxyl source.

17 Claims, No Drawings

COMPOSITION AND METHOD FOR BLEACHING A SUBSTRATE

FIELD OF INVENTION

This invention relates to compositions and methods for catalytically bleaching substrates with air or a peroxyl species using a defined class of ligand or complex as catalyst.

BACKGROUND OF INVENTION

The use of bleaching catalysts for stain removal has been developed over recent years. The recent discovery that some catalysts are capable of bleaching effectively in the absence of an added peroxyl source has recently become the focus of some interest, for example: WO9965905; WO0012667; WO0012808; WO0029537, and, WO0060045. The compounds found in the aforementioned application are, in many instances, also useful as bleach catalysts for use with peroxyl species.

The search for new classes of compounds that are suitable as air bleaching catalyst is ongoing. In addition, the selection within known groups for classes of compounds that are surprisingly effective as air bleaching catalysts and peroxyl bleaching catalysts is sought.

SUMMARY OF INVENTION

We have found that a selected class of ligand or complex is surprisingly effective in catalysing the bleaching of substrates using either air or a peroxyl species.

We have selected a group of ligands that are surprisingly effective as bleach catalysts. The ligand group selected has at least two imidazol groups as described herein.

The present invention provides a laundry bleach composition, capable of bleaching in an air bleaching mode or peroxyl bleaching mode, comprising a ligand of general formula (L):

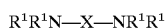 (L), wherein:
X is selected from —CH$_2$CH$_2$—, —CH$_2$CH$_2$CH$_2$—, —CH$_2$C(OH)HCH$_2$—; and,
R$^1$ independently represents a group selected from: alkyl, cycloalkyl, heterocycloalkyl, heteroaryl, aryl and arylalkyl groups optionally substituted with a substituent selected from hydroxy, alkoxy, phenoxy, carboxylate, carboxamide, carboxylic ester, sulphonate, amine, alkylamine and N$^+$ (R$^4$)$_3$, wherein R$^4$ is selected from hydrogen, alkanyl, alkenyl, arylalkanyl, arylalkenyl, oxyalkanyl, oxyalkenyl, aminoalkanyl, aminoalkenyl, alkanyl ether, alkenyl ether, and —CY$_2$—R$^2$, in which Y is independently selected from H, CH3, C2H5, C3H7 and R$^2$ is independently selected from: an optionally substituted:

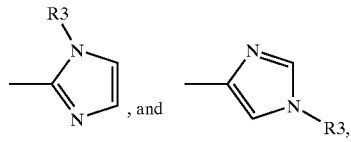

wherein R3 is independently selected from: H, alkyl, and benzyl, and wherein at least two of R$^1$ are —CY$_2$—R$^2$ and R$^2$. The optionally substituted imidazole is not so substituted that it forms a benzimidazol group per se.

It is essential that the ligand (L) has at least two imidazole substituents as defined above, preferably at least three imidazole substituents. The nature of the remaining R1 substituent(s) has not been found to be significant to activity of the selected ligand.

A present invention also provides a method of bleaching a substrate comprising applying to the substrate, in an aqueous medium, a bleaching composition as defined herein.

The present invention also extends to use of a ligand or complex as defined below in the manufacture of a bleaching composition, the bleaching composition containing effective amounts of a peroxygen bleach or a peroxy-based or peroxy-generating bleach system. An effective amount of a peroxygen bleach may be provided by a composition containing at least 1%, preferably at least 5%, of a peroxyl species. In the present invention, it is preferred that the composition contains the range of about 1–35% by weight, preferably from 5–25% of a peroxyl species.

The present invention also extends to a commercial package comprising a bleaching composition according to the present invention together with instructions for its use.

SUMMARY OF THE INVENTION

Air Bleaching Mode

In an air bleaching mode the composition of the present invention uses air to bleach a substrate. This is distinct from using pure oxygen or an enriched oxygen source. Air is different to molecular oxygen. The provision of a commercially available air bleaching product negates the requirement of an additional component, namely a peroxyl source. The removal of a peroxyl species, an expensive component, from a bleaching composition results in a reduction in manufacturing costs of the bleaching composition. Of significant importance is that an increased retention of textile strength and less dye damage is found when a bleaching composition without an added peroxyl species is used to clean fabrics. In addition, the provision of a commercially available air bleaching composition that may function without the requirement of saturated oxygen solutions and/or pressure vessels in an aqueous environment is important. Oxygen is relatively soluble in water when compared to organic solvents. Nitrogen makes up approximately 80% of the volume of air whilst molecular oxygen makes up only approximately 20% of the volume of air.

In the present invention at least 10%, preferably at least 50% and optimally at least 90% of any bleaching of the substrate is effected by oxygen sourced from the air.

In any composition containing organic matter it is difficult to avoid the presence of hydroperoxides which are readily formed from the oxygen in the air. In this regard, the air bleaching composition of the present invention has less that 1%, preferably less than 0.1%, most preferably less than 0.01%, of a peroxyl species present.

Peroxyl Bleaching Mode

The Peroxyl Species or Precursor Thereof

In a peroxyl bleaching mode the composition of the present invention uses a peroxyl species to bleach a substrate. The peroxy bleaching species may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 1–35% by weight, preferably from 5–25% by weight. One skilled in the art will appreciate that these amounts may be reduced in the presence of a bleach precursor e.g., N,N,N'N'-tetraacetyl ethylene diamine (TAED).

Another suitable hydrogen peroxide generating system is a combination of a C1–C4 alkanol oxidase and a C1–C4 alkanol, especially a combination of methanol oxidase (MOX) and ethanol. Such combinations are disclosed in International Application PCT/EP 94/03003 (Unilever), which is incorporated herein by reference.

Alkylhydroxy peroxides are another class of peroxy bleaching compounds. Examples of these materials include cumene hydroperoxide and t-butyl hydroperoxide.

Organic peroxyacids may also be suitable as the peroxy bleaching compound. Such materials normally have the general formula:

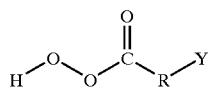

wherein R is an alkylene or substituted alkylene group containing from 1 to about 20 carbon atoms, optionally having an internal amide linkage; or a phenylene or substituted phenylene group; and Y is hydrogen, halogen, alkyl, aryl, an imido-aromatic or non-aromatic group, a COOH or

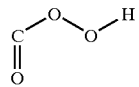

group or a quaternary ammonium group.

Typical monoperoxy acids useful herein include, for example:
(i) peroxybenzoic acid and ring-substituted peroxybenzoic acids, e.g. peroxy-.alpha.-naphthoic acid;
(ii) aliphatic, substituted aliphatic and arylalkyl monoperoxyacids, e.g. peroxylauric acid, peroxystearic acid and N,N-phthaloylaminoperoxy caproic acid (PAP); and
(iii) 6-octylamino-6-oxo-peroxyhexanoic acid.

Typical diperoxyacids useful herein include, for example:
(iv) 1,12-diperoxydodecanedioic acid (DPDA);
(v) 1,9-diperoxyazelaic acid;
(vi) diperoxybrassilic acid; diperoxysebasic acid and diperoxyisophthalic acid;
(vii) 2-decyldiperoxybutane-1,4-diotic acid; and
(viii) 4'-sulphonylbisperoxybenzoic acid.

Also inorganic peroxyacid compounds are suitable, such as for example potassium monopersulphate (MPS). If organic or inorganic peroxyacids are used as the peroxygen compound, the amount thereof will normally be within the range of about 2–10% by weight, preferably from 4–8% by weight.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are:

2-(N,N,N-trimethyl ammonium) ethyl sodium-4-sulphonphenyl carbonate chloride (SPCC);
N-octyl-N,N-dimethyl-N10-carbophenoxy decyl ammonium chloride (ODC);
3-(N,N,N-trimethyl ammonium) propyl sodium-4-sulphophenyl carboxylate; and
N,N,N-trimethyl ammonium toluyloxy benzene sulphonate.

A further special class of bleach precursors is formed by the cationic nitriles as disclosed in EP-A-303,520 and in European Patent Specification No. 's 458,396 and 464,880.

Any one of these peroxyacid bleach precursors can be used in the present invention, though some may be more preferred than others.

Of the above classes of bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of said preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl3-benzoloxy benzoate; SPCC; trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

Other classes of bleach precursors for use with the present invention are found in WO0015750, for example 6-(nonanamidocaproyl)oxybenzene sulphonate.

The precursors may be used in an amount of up to 12%, preferably from 2–10% by weight, of the composition.

The bleaching composition of the present invention has particular application in detergent formulations, especially for laundry cleaning. Accordingly, in another preferred embodiment, the present invention provides a detergent bleach composition comprising a bleaching composition as defined above and additionally a surface-active material, optionally together with detergency builder.

The bleach composition according to the present invention may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulphates and sulphonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those ethers of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolysing with a base to produce a random sulphonate; sodium and ammonium ($C_7$–$C_{12}$) dialkyl sulphosuccinates; and olefin sulphonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulphonates, and sodium ($C_{16}$–$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach composition of the invention will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps. The bleach composition of the present invention may also contain a detergency builder, for example in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Apart from the components already mentioned, the bleach composition of the present invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulphate and sodium silicate; and, usually in very small amounts, fluorescent agents; perfumes; enzymes, such as proteases, cellulases, lipases, amylases and oxidases; germicides and colourants.

Transition metal sequestrants such as EDTA, and phosphonic acid derivatives such as EDTMP (ethylene diamine tetra(methylene phosphonate) (same as dequest™ above) may also be included, in addition to the ligand specified, for example to improve the stability sensitive ingredients such as enzymes, fluorescent agents and perfumes, but provided the composition remains bleaching effective.

Additional Enzymes

The detergent compositions of the present invention may additionally comprise one or more enzymes, which provide cleaning performance, fabric care and/or sanitation benefits.

Said enzymes include oxidoreductases, transferases, hydrolases, lyases, isomerases and ligases. Suitable members of these enzyme classes are described in Enzyme nomenclature 1992: recommendations of the Nomenclature Committee of the International Union of Biochemistry and Molecular Biology on the nomenclature and classification of enzymes, 1992, ISBN 0-12-227165-3, Academic Press. The most recent information on the nomenclature of enzymes is available on the Internet through the ExPASy WWW server (http://www.expasy.ch/)

Examples of the hydrolases are carboxylic ester hydrolase, thiolester hydrolase, phosphoric monoester hydrolase, and phosphoric diester hydrolase which act on the ester bond; glycosidase which acts on O-glycosyl compounds; glycosylase hydrolysing N-glycosyl compounds; thioether hydrolase which acts on the ether bond; and exopeptidases and endopectidases which act on the peptide bond. Preferable among them are carboxylic ester hydrolase, glycosidase and exo- and endopeptidases. Specific examples of suitable hydrolases include (1) exopeptidases such as aminopeptidase and carboxypeptidase A and B and endopeptidases such as pepsin, pepsin B, chymosin, trypsin, chymotrypsin, elastase, enteropeptidase, cathepsin B, papain, chymopapain, ficain, thrombin, plasmin, renin, subtilisin, aspergillopepsin, collagenase, clostripain, kallikrein, gastricsin, cathepsin D, bromelain, chymotrypsin C, urokinase, cucumisin, oryzin, proteinase K, thermomycolin, thermitase, lactocepin, thermolysin, bacillolysin. Preferred among them is subtilisin; (2) glycosidases such as α-amylase, β-amylase, glucoamylase, isoamylase, cellulase, endo-1,3(4)-β-glucanase (β-glucanase), xylanase, dextranase, polygalacturonase (pectinase), lysozyme, invertase, hyaluronidase, pullulanase, neopullulanase, chitinase, arabinosidase, exocellobiohydrolase, hexosaminidase, mycodextranase, endo-1,4-β-mannanase (hemicellulase), xyloglucanase, endo-β-galactosidase (keratanase), mannanase and other saccharide gum degrading enzymes as described in WO-A-99/09127. Preferred among them are α-amylase and cellulase; (3) carboxylic ester hydrolase including carboxylesterase, lipase, phospholipase, pectinesterase, cholesterol esterase, chlorophyllase, tannase and wax-ester hydrolase. Preferred among them is lipase.

Examples of transferases and ligases are glutathione S-transferase and acid-thiol ligase as described in WO-A-98/59028 and xyloglycan endotransglycosylase as described in WO-A-98/38288.

Examples of lyases are hyaluronate lyase, pectate lyase, chondroitinase, pectin lyase, alginase II. Especially preferred is pectolyase, which is a mixture of pectinase and pectin lyase.

Examples of the oxidoreductases are oxidases such as glucose oxidase, methanol oxidase, bilirubin oxidase, catechol oxidase, laccase, peroxidases such as ligninase and those described in WO-A-97/31090, monooxygenase, dioxygenase such as lipoxygenase and other oxygenases as described in WO-A-99/02632, WO-A-99/02638, WO-A-99/02639 and the cytochrome based enzymatic bleaching systems described in WO-A-99/02641.

Peroxidases are used in combination with hydrogen peroxide, which can be formulated into a detergent composition as percarbonate or perborate. The hydrogen peroxide may also be generated during the washing and/or rinsing process by an enzymatic system as e.g. described in EP-A-537381.

The activity of oxidoreductases, in particular the phenol oxidising enzymes in a process for bleaching stains on fabrics and/or dyes in solution and/or antimicrobial treatment can be enhanced by adding certain organic compounds, called enhancers. Examples of enhancers are 2,2'-azo-bis-(3-ethylbenzo-thiazoline-6-sulphonate (ABTS) and Phenothiazine-10-propionate (PTP). More enhancers are described in WO-A-94/12619, WO-A-94/12620, WO-A-94/12621, WO-A-97/11217, WO-A-99/23887. Enhancers are generally added at a level of 0.01% to 5% by weight of detergent composition.

A different process for enhancing the efficacy of the bleaching action of oxidoreductases is by targeting them to stains by using antibodies or antibody fragments as described in WO-A-98/56885.

Antibodies can also be added to control enzyme activity as described in WO-A-98/06812.

A preferred combination is a detergent composition comprising of a mixture of conventional detergent enzymes such as protease, amylase, lipase, cutinase and/or cellulase together with one or more plant cell wall degrading enzymes.

Endopeptidases (proteolytic enzymes or proteases) of various qualities and origins and having activity in various pH ranges of from 4–12 are available and can be used in the instant invention. Examples of suitable proteolytic enzymes are the subtilisins, which can be obtained from particular strains of *B. subtilis, B. lentus, B. amyloliquefaciens* and *B. licheniformis*, such as the commercially available subtilisins Savinase™, Alcalase™, Relase™, Kannase™ and Everlase™ as supplied by Novo Industri A/S, Copenhagen, Denmark or Purafect™, PurafectOxP™ and Properase™ as supplied by Genencor International. Chemically or genetically modified variants of these enzymes are included such as described in WO-A-99/02632 pages 12 to 16 and in WO-A-99/20727 and also variants with reduced allergenicity as described in WO-A-99/00489 and WO-A-99/49056.

Suitable lipases include those of bacterial or fungal origin as described in WO-A-99/11770 pages 33, 34, such as the commercially available Lipolase™, Lipolase Ultra™, LipoPrime™, from Novo Nordisk, or Lipomax™ from Genencor. Chemically or genetically modified variants of these enzymes are included.

Suitable amylases include those of bacterial or fungal origin. Chemically or genetically modified variants of these enzymes are included as described in WO-A-99/02632 pages 18, 19. Commercial cellulase are sold under the tradename Purastar™, Purastar OxAm™ (formerly Purafact Ox Am™) by Genencor; Termamyl™, Fungamyl™ and Duramyl™, all available from Novo Nordisk A/S.

Suitable cellulases include those of bacterial or fungal origin. Chemically or genetically modified variants of these enzymes are included as described in WO-A-99/02632 page 17. Particularly useful cellulases are the endoglucanases such as the EGIII from *Trichoderma longibrachiatum* as described in WO-A-94/21801 and the E5 from *Thermomonospora fusca* as described in WO-A-97/20025. Endoglucanases may consist of a catalytic domain and a cellulose binding domain or a catalytic domain only. Preferred cellulolytic enzymes are sold under the tradename Carezyme™, Celluzyme™ and Endolase™ by Novo Nordisk A/S; Puradax™ is sold by Genencor and KAC™ is sold by Kao corporation, Japan.

Detergent enzymes are usually incorporated in an amount of 0.00001% to 2%, and more preferably 0.001% to 0.5%, and even more preferably 0.01% to 0.2% in terms of pure enzyme protein by weight of the composition. Detergent enzymes are commonly employed in the form of granules made of crude enzyme alone or in combination with other components in the detergent composition. Granules of crude enzyme are used in such an amount that the pure enzyme is 0.001 to 50 weight percent in the granules. The granules are used in an amount of 0.002 to 20 and preferably 0.1 to 3 weight percent. Granular forms of detergent enzymes are known as Enzoguard™ granules, prills, marumes or T-granules. Granules can be formulated so as to contain an enzyme protecting agent (e.g. oxidation scavengers) and/or a dissolution retardant material. Other suitable forms of enzymes are liquid forms such as the "L" type liquids from Novo Nordisk, slurries of enzymes in nonionic surfactants such as the "SL" type sold by Novo Nordisk and microencapsulated enzymes marketed by Novo Nordisk under the tradename "LDP" and "CC".

The enzymes can be added as separate single ingredients (prills, granulates, stabilised liquids, etc. containing one enzyme) or as mixtures of two or more enzymes (e.g. cogranulates). Enzymes in liquid detergents can be stabilised by various techniques as for example disclosed in U.S. Pat. Nos. 4,261,868 and 4,318,818.

The detergent compositions of the present invention may additionally comprise one or more biologically active peptides such as swollenin proteins, expansins, bacteriocins and peptides capable of binding to stains.

In a particularly preferred embodiment the method of the present invention is carried out on a laundry fabric using aqueous treatment liquor. In particular the treatment may be effected in, or as an adjunct to, an essentially conventional wash cycle for cleaning laundry. More preferably, the treatment is carried out in an aqueous detergent wash liquor. The bleaching composition can be delivered into the wash liquor from a powder, granule, pellet, tablet, block, bar or other such solid form. The solid form can comprise a carrier, which can be particulate, sheet-like or comprise a three-dimensional object. The carrier can be dispersible or soluble in the wash liquor or may remain substantially intact. In other embodiments, the bleaching composition can be delivered into the wash liquor from a paste, gel or liquid concentrate. Other means for ensuring that the bleaching composition is present in the wash liquor may be envisaged.

For example, it is envisaged that the bleaching composition can be presented in the form of a body from which it is slowly released during the whole or part of the laundry process. Such release can occur over the course of a single wash or over the course of a plurality of washes. In the latter case it is envisaged that the bleaching composition can be released from a carrier substrate used in association with the wash process, e.g. from a body placed in the dispenser drawer of a washing machine, elsewhere in the delivery system or in the drum of the washing machine. When used in the drum of the washing machine the carrier can be freely moving or fixed relative to the drum. Such fixing can be achieved by mechanical means, for example by barbs that interact with the drum wall, or employ other forces, for example a magnetic force. The modification of a washing machine to provide for means to hold and retain such a carrier is envisaged similar means being known from the analogous art of toilet block manufacture. Freely moving carriers such as shuttles for dosage of surfactant materials and/or other detergent ingredients into the wash can comprise means for the release of the bleaching composition into the wash.

The present invention is not limited to those circumstances in which a washing machine is employed, but can be applied where washing is performed in some alternative vessel. In these circumstances it is envisaged that the bleaching composition can be delivered by means of slow release from the bowl, bucket or other vessel which is being employed, or from any implement which is being employed, such as a brush, bat or dolly, or from any suitable applicator.

Suitable pre-treatment means for application of the bleaching composition to the textile material prior to the main wash include sprays, pens, roller-ball devices, bars, soft solid applicator sticks and impregnated cloths or cloths containing microcapsules. Such means are well known in the analogous art of deodorant application and/or in spot treatment of textiles. Similar means for application are employed in those embodiments where the bleaching composition is applied after the main washing and/or conditioning steps have been performed, e.g. prior to or after ironing or drying of the cloth. For example, the bleaching composition may be applied using tapes, sheets or sticking plasters coated or impregnated with the substance, or containing microcapsules of the substance. The bleaching composition may for example be incorporated into a drier sheet so as to be activated or released during a tumble-drier cycle, or the substance can be provided in an impregnated or microcapsule-containing sheet so as to be delivered to the textile when ironed.

Throughout the description and claims generic groups have been used, for example alkyl, alkoxy, aryl. Unless otherwise specified the following are preferred group restrictions that may be applied to generic groups found within compounds disclosed herein:

alkyl: linear and branched C1–C8-alkyl, alkenyl: C2–C6-alkenyl, cycloalkyl: C3–C8-cycloalkyl, aryl: selected from homoaromatic compounds having a molecular weight under 300, heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithia-cyclononanyl; tetrahydropyranyl; and oxazolidinyl, wherein the heterocycloalkyl may be connected to the compound via any atom in the ring of the selected heterocycloalkyl, carboxylate derivative: the group —C(O)OR, wherein R is selected from: hydrogen; C1–C6-alkyl; phenyl; C1–C6-alkyl-C6H5; Li; Na; K; Cs; Mg; and Ca, carbonyl derivative: the group —C(O)R, wherein R is selected from: hydrogen; C1–C6-alkyl; phenyl; C1–C6-alkyl-C6H5 and amine (to give amide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, sulphonate: the group —S(O)$_2$OR, wherein R is selected from: hydrogen; C1–C6-alkyl; phenyl; C1–C6-alkyl-C6H5; Li; Na; K; Cs; Mg; and Ca, Unless otherwise specified the following are more preferred group restrictions that may be applied to groups found within compounds disclosed herein:

alkyl: linear and branched C1–C6-alkyl, alkenyl: C3–C6-alkenyl, cycloalkyl: C6–C8-cycloalkyl, aryl: selected from group consisting of: phenyl; biphenyl; naphthalenyl; anthracenyl; and phenanthrenyl, heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl, carboxylate derivative: the group —C(O)OR, wherein R is selected from hydrogen; Na; K; Mg; Ca; C1–C6-alkyl; and benzyl, The invention will now be further illustrated by way of the following non-limiting examples:

EXAMPLES

Syntheses of Compounds

[(MeN4Py) FeCl]Cl

The ligand N,N-bis(pyridin-2-yl-methyl)-1,1-bis(pyridin-2-yl)-1-aminoethane (MeN4py) was prepared as described in EP 0 909 809 A2.

The ligand MeN4Py (33.7 g; 88.5 mmoles) was dissolved in dry methanol (500 ml). Small portions of $FeCl_2.4H_2O$ (0.95 eq; 16.7 g; 84.0 mmoles) were added, yielding a clear red solution. After addition, the solution was stirred for 30 minutes at room temperature, after which the methanol was removed (rotary-evaporator). The dry solid was ground and 150 ml of ethylacetate was added and the mixture was stirred until a fine red powder was obtained. This powder was washed twice with ethyl acetate, dried in the air and further dried under reduced pressure vacuum at 40° C. El. Anal. Calc. for $[Fe(MeN4py)Cl]Cl.2H_2O$: C 53.03; H 5.16; N 12.89; Cl 13.07; Fe 10.01%. Found C 52.29/52.03; H 5.05/5.03; N 12.55/12.61; Cl: 12.73/12.69; Fe: 10.06/10.01%.

L1 has been prepared according to literature procedures (Bernal, J.; et al. J. Chem. Soc., Dalton Trans. 1995, 3667–3675). L10 has been prepared according to literature procedures (Brennan, et al., Inorg. Chem., 30, 1937 (1991).

Reaction Procedure for Ligands L2, L3, L4, L5, L6, L7, L8, and L9.

The general procedure of these ligands is as follows. To a 25 ml glass vial was added the ethylenediamine (1 mmol), and aldehyde (4 mmol).

The following commercially available ethylene diamines were used for the ligand syntheses:

L2: N-methylethylenediamine;
L3: N-ethyl-ethylenediamine;
L4: N,N'-dimethylethylenediamine;
L5 and L6: N-(1-propan-2ol )ethylenediamine;
L7: N,N-diethyldiethylenetriamine;
L8: N-3-propan-1-ol)ethylenediamine;
L9: N-hexylethylenediamine.

The following commercially available aldehydes were used for the ligand syntheses:

L2, L3, L4, and L5: 2-imidazolecarboxaldehyde;
L6, and L8: 1-methyl-2-imidazolecarboxaldehyde;
L7: 5-methyl-imidazol-4-methylcarboxaldehyde
L9 4-formylimidazole The above-mentioned vial was sealed with a cap and the solution was then shaken for 2 h to allow the imine formation. The mixture was treated with $NaCNBH_3$ (3.3 mmol), adjusted to pH 6 with acetic acid and shaken for 38 h. The mixture was quenched with 3 ml of 2 M HCl solution and adjusted to pH>13 with a 7M NaOH solution. The mixture was extracted with 3×10 ml of dichloromethane, dried over sodium sulfate and evaporated under reduced pressure. Yields are typically around 50%. Purities are greater than 90% as established by HPLC/MS.

L2: m/z 315.5 $(M+H^+)$
L3: m/z 329.4 $(M+H^+)$
L4: m/z 249.3 $(M+H^+)$
L5: m/z 359.5 $(M+H^+)$
L6: m/z 401.5 $(M+H^+)$
L7: m/z 443.5 $(M+H^+)$
L8: m/z 401.5 $(M+H^+)$
L9: m/z 385.5 $(M+H^+)$

Tomato Stain Bleaching

In an aqueous solution containing 10 mM carbonate buffer (pH 10) with 0.6 g/l NaLAS (linear alkylbenzene sulfonate), tomato-soya oil stained cloths were added and kept in contact with the solution under agitation for 30 minutes at 30 ° C. In comparative experiments, the same experiments were done by addition of 10 μM of compound 1, or 10 μM of transition-metal salt in combination with 20 μM ligand (L1-L10), or the ligand alone without addition of metal salts (L1–L10) referred to in the table below.

After the wash, the cloths were rinsed with water and subsequently dried at 30° C. and the change in colour was measured immediately after drying with a Linotype-Hell scanner (ex Linotype) ("t=0") and after 1 day storage in the dark ("t=1"). The change in colour (including bleaching) is expressed as the ΔE value. The measured colour difference (ΔE) between the washed cloth and the unwashed cloth is defined as follows:

$$\Delta E=[(\Delta L)^2+(\Delta a)^2+(\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormetry, Bureau Central de la CIE, Paris 1978. The results are shown below in the Table below.

| | t = 0 | t = 1 |
|---|---|---|
| Blank | 16 | 16 |
| $FeMeN4pyCl_2$ | 5 | 4 |
| MeN4py/Fe perchlorate | 7 | 5 |
| COMPARITIVE EXAMPLE (NO IMIDAZOLE GROUPS) | | |
| N-methyl-N,N',N'-tris(pyridin-2ylmethyl)ethylenediamine (L1) | 8 | 10 |
| L1+ Fe perchlorate | 9 | 9 |
| L1+ Cu perchlorate | 13 | 13 |
| L1+ Co perchlorate | 10 | 7 |
| N-Methyl-N,N',N'-Tris(imidazol-2ylmethyl)-ethylenediamine (L2) | 2 | 2 |
| L2+ Fe perchlorate | 3 | 3 |
| L2+ Cu perchlorate | 5 | 4 |
| L2+ Mn perchlorate | 7 | 5 |
| L2+ Co perchlorate | 15 | 4 |
| N-ethyl-N,N',N'-Tris(imidazol-2ylmethyl)-ethylenediamine (L3) | 3 | 3 |
| L3 Fe perchlorate | 3 | 3 |
| L3 Cu perchlorate | 4 | 5 |
| L3 Mn perchlorate | 7 | 5 |
| L3 Co perchlorate | 6 | 5 |
| N,N'-dimethyl-N,N'-bis(imidazol-2-ylmethyl)-ethylenediamine (L4) | 12 | 3 |
| N-(1-propan-2-ol)-N,N',N'-Tris(imidazol-2ylmethyl)-ethylenediamine (L5) | — | 3 |
| L5 + Fe perchlorate | — | 5 |
| L5+ Cu perchlorate | — | 4 |
| L5+ Mn perchlorate | — | 4 |
| L5+ Co perchlorate | — | 4 |

-continued

| | t = 0 | t = 1 |
|---|---|---|
| N-(1-propan-2-ol)-N,N',N'-Tris(1-methyl-imidazol-2ylmethyl)-ethylenediamine (L6) | 5 | 3 |
| L6 + Fe perchlorate | — | 5 |
| L6+ Cu perchlorate | — | 4 |
| L6+ Mn perchlorate | — | 5 |
| L6+ Co perchlorate | 14 | 4 |
| N,N-diethyl-N',N'',N'''-Tris(5-methyl-imidazol-4ylmethyl)-diethylenetriamine (L7) | — | — |
| L7 + Fe perchlorate | — | — |
| L7+ Cu perchlorate | 13 | 8 |
| L7+ Mn perchlorate | 14 | 8 |
| L7+ Co perchlorate | 14 | 6 |
| N-(3-propan-1-ol)-N,N',N'-Tris(1-methyl-imidazol-2ylmethyl)-ethylenediamine (L8) | 4 | 3 |
| L8 + Fe perchlorate | 4 | — |
| L8+ Cu perchlorate | 5 | 3 |
| L8+ Mn perchlorate | — | 3 |
| L8+ Co perchlorate | 11 | 3 |
| N-hexyl-N,N',N'-Tris(imidazol-2ylmethyl)-ethylenediamine (L9) | 9 | 6 |
| L9 + Fe perchlorate | — | — |
| L9+ Cu perchlorate | 12 | 9 |
| L9+ Mn perchlorate | 14 | 7 |
| L9+ Co perchlorate | 13 | 6 |

The following table illustrates the present invention in peroxyl bleaching mode. The experiments were conducted in substantially the same manner as described above but in the presence of 10 mmol/l hydrogen peroxide. All data given were obtained immediately after the wash. AE measurements are given with respect to white.

| | ΔE |
|---|---|
| Blank | 16 |
| FeMeN4pyCl₂ | 5 |
| COMPARITIVE EXAMPLE (NO IMIDAZOLE GROUPS) | |
| N,N,N',N'-tetrakis(pyridin-2ylmethyl)ethylenediamine (L10) | 8 |
| N-Methyl-N,N',N'-Tris(imidazol-2ylmethyl)-ethylenediamine (L2) | 2 |
| L2+ Fe perchlorate | 3 |
| L2+ Cu perchlorate | 3 |
| L2+ Mn perchlorate | 2 |
| L2+ Co perchlorate | 3 |
| N-ethyl-N,N',N'-Tris(imidazol-2ylmethyl)-ethylenediamine (L3) | 3 |
| L3 Fe perchlorate | 2 |
| L3 Cu perchlorate | 2 |
| L3 Mn perchlorate | 2 |
| L3 Co perchlorate | 3 |
| N-(1-propan-2-ol)-N,N',N'-Tris(1-methyl-imidazol-2ylmethyl)-ethylenediamine (L6) | 4 |
| L6 + Fe perchlorate | 7 |
| L6 + Cu perchlorate | 8 |
| L6 + Mn perchlorate | 7 |
| L6 + Co perchlorate | 7 |
| N-(3-propan-1-ol)-N,N',N'-Tris(1-methyl-imidazol-2ylmethyl)-ethylenediamine (L8) | 3 |
| L8 + Fe perchlorate | 4 |
| L8+ Cu perchlorate | 7 |
| L8+ Mn perchlorate | 2 |
| L8+ Co perchlorate | 3 |

The above tabulated results demonstrate a substantial advantage secured by the selected group of compounds in both air bleaching and bleaching with peroxyl species.

We claim:

1. A laundry bleach composition, capable of bleaching in an air bleaching mode or peroxyl bleaching mode, comprising a ligand of general formula (L):

$$R^1R^1N-X-NR^1R^1 \qquad (L),$$

wherein:

X is selected from —CH₂CH₂—, —CH₂CH₂CH₂—, —CH₂C(OH)HCH₂—; and, $R^1$ independently represents a group selected from: alkyl, cycloalkyl, heterocycloalkyl, heteroaryl, aryl and arylalkyl groups optionally substituted with a substituent selected from hydroxy, alkoxy, phenoxy, carboxylate, carboxamide, carboxylic ester, sulphonate, amine, alkylamine and $N^+(R^4)_3$, wherein $R^4$ is selected from hydrogen, alkanyl, alkenyl, arylalkanyl, arylalkenyl, oxyalkanyl, oxyalkenyl, aminoalkanyl, aminoalkenyl, alkanyl ether, alkenyl ether, and —CY₂—R², in which Y is independently selected from H, CH3, C2H5, C3H7 and $R^2$ is independently selected from: an optionally substituted:

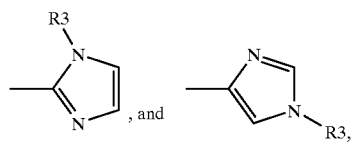

wherein R3 is independently selected from: H, alkyl, and benzyl, and wherein at least two of $R^1$ are —CY₂—R² and $R^2$ is not so substituted to form a benzimidazol group.

2. A bleaching composition according to claim 1, wherein R3 is independently selected from: H and methyl.

3. A bleaching composition according to claim 1, wherein the substituent of the optionally substituted:

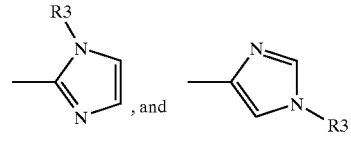

is selected from: CH3, C2H5, C3H7 C4H9, and CH2—C6H5.

4. A bleaching composition to claim 1, wherein $R^2$ is independently selected from:

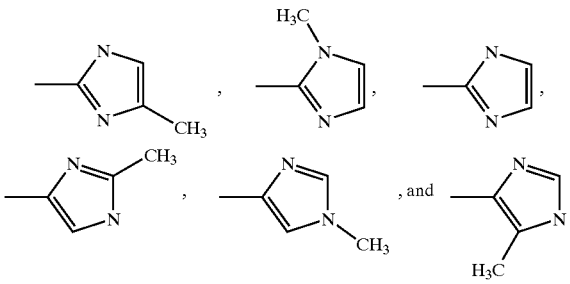

5. A bleaching composition according to claim 4, wherein $R^2$ is independently selected from:

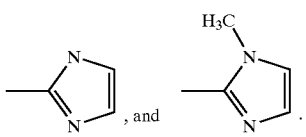, and.

6. A bleaching composition according to claim 1, wherein all —CY$_2$—R$^2$ are identical.

7. A bleaching composition according to claim 1, wherein at least three of R$^1$ are —CY$_2$—R$^2$.

8. A bleaching composition according to claim 1, wherein X is —CH$_2$CH$_2$—.

9. A bleaching composition according to claim 1, wherein the ligand is selected from N-Methyl-N,N',N'-Tris(imidazol-2ylmethyl)-ethylenediamine; N-ethyl-N,N',N'-Tris(imidazol-2-ylmethyl)-ethylenediamine; N,N'-dimethyl-N,N'-bis(imidazol-2-ylmethyl)-ethylenediamine; N-(1-propan-2-ol)-N,N',N'-Tris(imidazol-2ylmethyl)-ethylenediamine; N-(1-propan-2-ol)-N,N',N'-Tris(1-methyl-imidazol-2ylmethyl)-ethylenediamine; N,N-diethyl-N',N'',N''-Tris(5-methyl-imidazol-4ylmethyl)-diethylenetriamine; N-(3-propan-1-ol)-N,N',N'-Tris(1-methyl-imidazol-2ylmethyl)-ethylenediamine; and, N-hexyl-N,N',N'-Tris(imidazol-2ylmethyl)-ethylenediamine.

10. A bleaching composition according to claim 1, wherein the ligand of general formula (L) is present in the form of a complex of the general formula (A):

[LMX$_n$]Y$_q$      (A)

in which

M represents iron in the II, III, IV or V oxidation state, manganese in the II, III, IV, VI or VII oxidation state, copper in the I, II or III or cobalt in the I, II or III oxidation state;

X represents a coordinating species;

n represents zero or an integer in the range from 0 to 3;

z represents the charge of the complex and is an integer which can be positive, zero or negative;

Y represents a counter ion, the type of which is dependent on the charge of the complex;

q=z/[charge Y].

11. A bleaching composition according to claim 1, wherein the composition comprises a surface-active material and a detergency builder.

12. A bleaching composition according to claim 1, wherein in an aqueous solution at least 10%, of any bleaching of a substrate is effected by oxygen sourced from the air.

13. A bleaching composition according to claim 1, further comprising a sequestrant and wherein in an aqueous solution at least 90% of any bleaching of the substrate is effected by a peroxyl species not derived directly from atmospheric oxygen.

14. A method of bleaching a substrate comprising the step of applying to the substrate, in an aqueous medium, a bleaching composition as defined in claim 1.

15. A ligand selected from the group consisting of: N-Methyl-N,N',N'-Tris(imidazol-2ylmethyl)-ethylenediamine; N-ethyl-N,N',N'-Tris(imidazol-2ylmethyl)-ethylenediamine; N,N'-dimethyl-N,N'-bis(imidazol-2-ylmethyl)-ethylenediamine; N-(1-propan-2-ol)-N,N',N'-Tris(imidazol-2ylmethyl)-ethylenediamine; N-(1-propan-2-ol)-N,N',N'-Tris(1-methyl-imidazol-2ylmethyl)-ethylenediamine; N,N-diethyl-N',N'',N''-Tris(5-methyl-imidazol-4ylmethyl)-diethylenetriamine; N-(3-propan-1-ol)-N,N',N'-Tris(1-methyl-imidazol-2ylmethyl)-ethylenediamine; and N-hexyl-N,N',N'-Tris(imidazol-2ylmethyl)-ethylenediamine.

16. A bleaching composition according to claim 1, wherein in an aqueous solution at least 50% of any bleaching of a substrate is effected by oxygen sourced from the air.

17. A bleaching composition according to claim 1, wherein in an aqueous solution at least 90% of any bleaching of a substrate is effected by oxygen sourced from the air.

* * * * *